United States Patent
Alfaro et al.

[11] Patent Number: 5,184,354
[45] Date of Patent: Feb. 9, 1993

[54] PROTECTIVE HEAD AND EYE GEAR

[75] Inventors: Daniel V. Alfaro; Cecilio V. Jimenez, Jr., both of Corpus Christi, Tex.

[73] Assignee: AlJim Corporation, Corpus Christi, Tex.

[21] Appl. No.: 705,347

[22] Filed: May 24, 1991

[51] Int. Cl.⁵ ............................................. A61F 9/02
[52] U.S. Cl. ................................................ 2/425; 2/9; 2/431; 2/433; 2/452
[58] Field of Search .................. 2/425, 431, 433, 424, 2/10, 421, 426, 427, 452, 9

[56] References Cited

U.S. PATENT DOCUMENTS

| | | | |
|---|---|---|---|
| 427,438 | 5/1890 | McConihay | 2/431 |
| 1,716,550 | 6/1929 | Hart | 2/9 |
| 2,212,945 | 8/1940 | Lehrfeld | 2/433 |
| 2,395,078 | 2/1946 | Sowle | 2/9 |
| 2,546,842 | 3/1951 | Yealdhall | 2/425 |
| 2,715,222 | 8/1955 | Sowle | 2/9 |
| 3,992,722 | 11/1976 | Rhee | 2/425 |
| 4,222,122 | 9/1980 | Toms | 2/9 |
| 4,229,837 | 10/1980 | Solari | 2/431 |
| 4,617,686 | 10/1986 | Nahas | 2/433 |
| 4,831,665 | 5/1989 | Palmaer | 2/433 X |
| 5,012,527 | 5/1991 | Michel | 2/9 |

Primary Examiner—Peter Nerbun
Attorney, Agent, or Firm—G. Turner Moller

[57] ABSTRACT

Headgear for athletes such as basketball players includes a head encircling strap assembly and an eye/nose protective assembly. The strap assembly includes straps extending around the user's head and under the chin and provides padding at strategic places. The eye/nose assembly includes an eye encircling rim connected to the strap assembly and a covering over the rim to protect the user's eyes. The covering is preferably a filament mesh grid using filaments less than about 0.050" in diameter spaced not more than about ⅜ inch apart.

11 Claims, 1 Drawing Sheet

U.S. Patent
Feb. 9, 1993
5,184,354
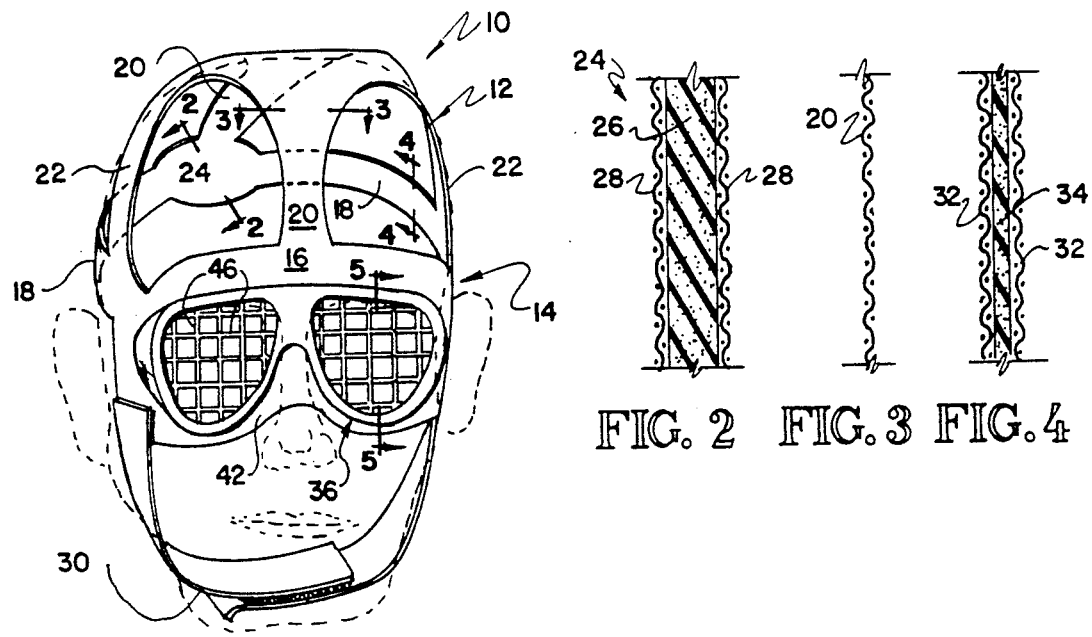
FIG. 1
FIG. 2  FIG. 3  FIG. 4
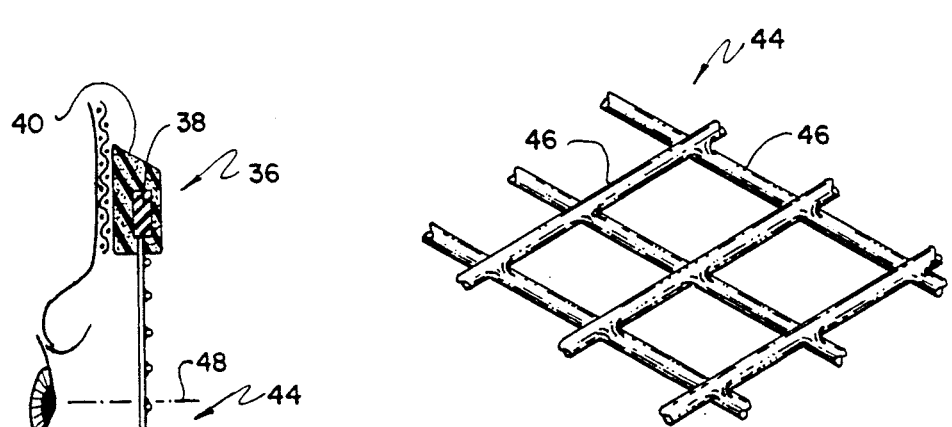
FIG. 5  FIG. 6
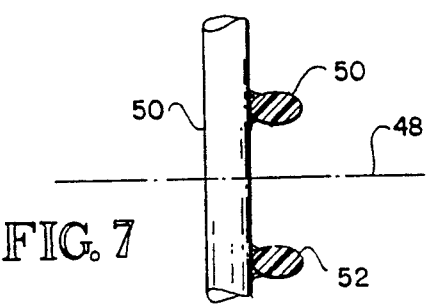
FIG. 7

PROTECTIVE HEAD AND EYE GEAR

This invention relates to a protective gear and, more particularly, a head and/or eye protective device.

Helmets are commonly worn in sports where the risk of injury is high. Football, motorcycling, bicycling, and other high speed sports have evolved helmets uniquely suitable to the risks of the particular sport. Masks or eye protective devices are also common in sports where eye or face injuries are probable. Thus, masks have been devised for baseball catchers, squash players, racquetball players, fencers and the like.

Disclosures of interest relative to this invention are found in U.S. Pat. Nos. 924,613; 4,185,331; 4,494,251; 4,173,795; 4,847,921 and 4,912,777.

The only protective device worn by basketball players are goggles covering the eyes and upper part of the nose with an elastic strap extending under the maximum circumference of the skull. While such devices act to minimize eye and socket injuries, they leave much to be desired and a number of improvements are envisioned by this invention.

It is an object of this invention to provide an improved combination headgear and mask for protecting the eyes, eye sockets, nose and head of a wearer, particularly a basketball player.

Another object of this invention is to provide an improved combination headgear and mask for a basketball player.

These and other objects of this invention will become more fully apparent as this description proceeds, reference being made to the accompanying drawing and appended claims.

IN THE DRAWINGS:

FIG. 1 is a slightly offset front view of the headgear of this invention;

FIG. 2 is an enlarged cross-sectional view of the headgear of FIG. 1, taken substantially along line 1—1, as viewed in the direction indicated by the arrows;

FIG. 3 is an enlarged cross-sectional view of the headgear of FIG. 1, taken substantially along line 3—3 thereof, as viewed in the direction indicated by the arrows;

FIG. 4 is an enlarged cross-sectional view of the headgear of FIG. 1, taken substantially along line 4—4 thereof, as viewed in the direction indicated by the arrows;

FIG. 5 is an enlarged cross-sectional view of the headgear of FIG. 1, taken substantially along line 5—5 thereof, as viewed in the direction indicated by the arrows;

FIG. 6 is a partial isometric view of the mesh or grid extending across the eyepiece of this invention; and FIG. 7 is an enlarged cross-sectional view of another embodiment of the filamentary structure of this invention.

Referring to FIGS. 1-5, a headgear 10 of this invention includes, as major components, a head encircling strap assembly 12 and an eye/nose protective assembly 14. The strap assembly 12 includes a wide forehead band 16 on the user's forehead above the eye brows, a head encircling strap 18 connected to the forehead band 16 and extending about the maximum circumference of the user's head and a top strap 20 extending from the forehead band 16 to the back of the head encircling strap 18. In addition, one or more lateral top straps 22 connect the top strap 20 and the head encircling strap 18. The top straps 20, 22 keep the head encircling strap 18 more-or-less on the maximum circumference of the user's head.

The strap assembly 12 also includes a large pad 24 at the intersection of the head encircling strap 1 and the top strap 20. As shown in FIG. 2, the pad 24 includes a layer of foam or other padding material 26 sandwiched between a pair of outer layers 28 to protect the user's head, during a fall, from contact with the basketball court.

The strap assembly 12 also includes a chin strap 30 connected to the head encircling strap 18 and/or the forehead band 16 in any suitable manner, as by sewing or VELCRO. The chin strap 30 extends downwardly from both sides of the headgear 10 under the user's chin and stabilizes the front of the strap assembly 12 and the eye/nose protective assembly 14. The chin strap 30 may be elastic or may include a buckle or VELCRO faster at the ends.

The top straps 20, 22 are preferably made of a light weight, unpadded fabric material as shown in FIG. 3. The head encircling strap 18 may be made of the same material but preferably is of a heavier material including a padded layer 32 sandwiched between a pair of outer layers 34, as shown in FIG. 4.

As shown in FIGS. 1 and 5, the eye/nose protective assembly 14 includes an eye encircling rim 36 including a more-or-less rigid member 38 encapsulated in foam or other suitable padding material 40. The upper part of the rim 36 abuts the user's forehead above the eyebrows and connects to the forehead band 16 in any suitable manner, as by stitching or gluing. The lower part of the rim 36 rests on the user's eye sockets, cheekbone and nose and connects to a band 42 extending laterally across the user's face and connecting to the chin straps 30.

The covering over the rim 36 may comprise a clear plastic lens much like conventional goggles. Preferably, the rim 36 is spanned by a filamentary structure 44 comprising a multiplicity of fine filaments 46 in a grid. The filaments 46 should be sufficiently close together to prevent a human finger from passing between them. By securing the filaments 46 together at the intersections thereof, as by bonding or gluing, the filamentary grid is stabilized so the filaments 46 do not spread apart when encountering a small object, such as the end of a finger. Securing the filaments 46 together at the intersections also greatly strengthens the grid and the filaments 44 can be made small enough and spaced apart far enough not to interfere seriously with visibility.

Although the filaments 46 may be of any suitable cross-section, circular is much preferred for a number of reasons, one of which is simplicity, although oval or polygonal shapes also work and can provide additional advantages. From a vision viewpoint, an important consideration is the dimension of the filaments 46 perpendicular or transverse to the line of sight 48 because material extending in this direction obscures vision more than material parallel to the line of sight 48. Thus, filaments 50, FIG. 7, of oval or elongate cross-section with the short dimension perpendicular to the line of sight provide improved visibility through the filamentary structure 44 without loss of strength.

For round filaments, it has been found that if the filaments 46 are less than about 0.075" and preferably less than about 0.050" in diameter and spaced apart in a grid not less than about $\frac{3}{8}$" on centers, the user does not substantially notice the vision impediment or, if the user does notice, practice with the headgear 10 shortly allows the athlete to operate as if there is no vision impairment. The filaments 50 with an elongate cross-section may have a slightly smaller short dimension than the diameter of circular filaments because much of the strength giving material is parallel to the line of sight 48 and thus does not obscure vision incrementally.

Although the filaments 46 may be of many different materials, a preferred group of materials is thermoplastic organic polymeric compounds such as NYLON, polypropylene and the like. These materials can be readily formed of any desired shape and secured together at the intersections by relatively simple thermal bonding techniques.

Although this invention has been disclosed and described in its preferred forms with a certain degree of particularity, it is understood that the present disclosure of the preferred forms is only by way of example and that numerous changes in the details of operation and in the combination and arrangement of parts may be resorted to without departing from the spirit and scope of the invention as hereinafter claimed.

I claim:

1. A combination head and eye protective headgear, comprising:

a head encircling strap assembly including a bodily flexible forehead band of unpadded material for extending horizontally above the eyebrows of the user, a bodily flexible head encircling strap of padded material connected to the forehead band for extending horizontally around the user's head near its maximum periphery, a bodily flexible top strap of unpadded material connected tot he forehead band for extending vertically over the top of the user's head and connected to the head encircling strap near its rearmost extremity, a bodily flexible chin strap and means connecting the chin strap to the head encircling strap assembly for extending below the chin of the user; and an eye protective assembly connected to the forehead band and to the chin strap and terminating above the end of the user's nose, the eye protective assembly including a bodily flexible unpadded band for extending across the user's nose, a padded eye encircling rim having an annular relatively rigid frame and padding material encapsulating the annular frame.

2. The combination head and eye protective headgear of claim 1 wherein the head encircling strap and the top strap intersect at a first location adjacent the rear of the headgear and the padding member comprises an enlargement at the first location.

3. The combination head and eye protective headgear of claim 1 wherein the eye protective assembly comprises a clear transparent rigid member.

4. The combination head and eye protective headgear of claim 1 wherein the eye protective assembly comprises a mesh of filaments.

5. The combination head and eye protective headgear of claim 4 wherein the eye protective assembly provides a line of sight from a user away form the headgear and the filaments are of a cross-sectional shape having a dimension perpendicular to the line of sight less than about 0.075" in a grid not more than about ⅜" on centers.

6. The combination head and eye protective headgear of claim 5 wherein the filaments are of circular cross section.

7. The combination head and eye protective headgear of claim 6 wherein the circular filaments are no larger than about 0.050" in diameter.

8. The combination head and eye protective headgear of claim 5 wherein the filaments in the grid comprise a first group of filaments extending in one direction and a second group of filaments extending in a second direction transverse to the first direction and abutting the first group of filaments at a multiplicity of intersections, the filaments of the first and 9. The combination head and eye protective gear of claim 1 wherein the unpadded material is unpadded fabric.

10. The combination head and eye protective gear of claim 9 wherein the padded material comprises two layers of unpadded fabric having a foam rubber layer therebetween.

11. The combination head and eye protective gear of claim 5 wherein the filaments are of a non-circular cross-section having a long dimension parallel to the line of sight and a short dimension perpendicular to the light of sight.

* * * * *